United States Patent
Beguelin et al.

(10) Patent No.: US 10,648,991 B2
(45) Date of Patent: May 12, 2020

(54) BIOMARKERS FOR EPICARDIAL ADIPOSE TISSUE

(71) Applicant: Nestec S.A., Vevey (CH)

(72) Inventors: Fiona Camille Beguelin, Lausanne (CH); Sebastiano Collino, Lausanne (CH); François-Pierre Martin, Vuisternens-devant-Romont (CH); Ivan Montoliu Roura, Lausanne (CH); Max Scherer, Ottobrunn (DE)

(73) Assignee: Societe des Produits Nestle S.A., Vevey (CH)

( * ) Notice: Subject to any disclaimer, the term of this patent is extended or adjusted under 35 U.S.C. 154(b) by 101 days.

(21) Appl. No.: 15/102,490

(22) PCT Filed: Dec. 9, 2014

(86) PCT No.: PCT/EP2014/077038
§ 371 (c)(1),
(2) Date: Jun. 7, 2016

(87) PCT Pub. No.: WO2015/104113
PCT Pub. Date: Jul. 16, 2015

(65) Prior Publication Data
US 2016/0305968 A1 Oct. 20, 2016

(30) Foreign Application Priority Data

Jan. 8, 2014 (EP) .................................. 14150452

(51) Int. Cl.
*G01N 33/92* (2006.01)
*A23L 33/00* (2016.01)
*G09B 19/00* (2006.01)

(52) U.S. Cl.
CPC .............. *G01N 33/92* (2013.01); *A23L 33/30* (2016.08); *G09B 19/00* (2013.01);
(Continued)

(58) Field of Classification Search
CPC ........ G01N 33/92; G01N 33/48; A23L 33/30; G01B 19/00; G01B 19/0092
See application file for complete search history.

(56) References Cited

U.S. PATENT DOCUMENTS

2013/0023054 A1* 1/2013 Meikle .................. G01N 33/92
436/71

FOREIGN PATENT DOCUMENTS

CN 102209894 A 10/2011
JP 2010519543 A 6/2010
(Continued)

OTHER PUBLICATIONS

Bottom Up Shotgun Lipidomics by Higher Energy Collisional Dissociation on LTQ Orbittrap Mass Spectrometers Kai Schuhmann, Ronny Herzog, Dominik Schwudke, Wolfgang Metelmann-Strupat, Stefan R. Bornstein, and Andrej Shevchenko Anal. Chem. 2011, 83, 5480-5487.*

(Continued)

*Primary Examiner* — Krishnan S Menon
*Assistant Examiner* — Dwan A Gerido
(74) *Attorney, Agent, or Firm* — K&L Gates LLP

(57) ABSTRACT

A method for predicting the level of epicardial adipose tissue (EAT) in a subject comprising: (a) determining a level of one or more lipid biomarkers in a sample from the subject, wherein the biomarkers are selected from the following: (i) phosphatidylcholine (PC) [16:1/16:1] (ii) diacylglycerol (DAG) [42:8] (iii) phosphatidylethanolamine-ether (PE-O) [32:5] (iv) phosphatidylcholine (PC) [18:0/22:5] (v) phosphatidylinositol (PI) [18:0/16:1] (vi) phosphatidylglycerol (PG) [20:3/20:3] (vii) phosphatidylglycerol (PG) [22:5/18:1] (b) comparing the levels of the biomarkers in the sample to reference values; wherein the levels of the biomarkers in (Continued)

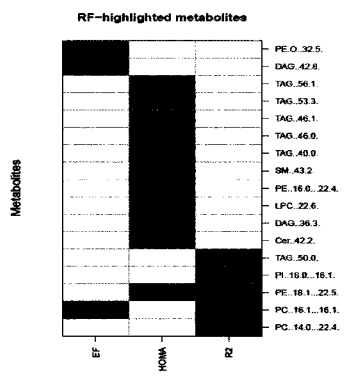

Summary of Relevant Variables for predicting Epicardial fat, Insulin resistance and Visceral adiposity. Legend: EF, Epicardial fat; HOMA, HOMA-IR; R2, Visceral adiposity. The table lists metabolite importance and robustness in predicting epicardial fat, visceral fat and HOMA-IR as assessed by Random forest analysis. Pooled mean decrease in accuracy after n=10000 random forest generations.

the sample compared to the reference values are indicative of levels of EAT fat in the subject.

22 Claims, 1 Drawing Sheet

(52) U.S. Cl.
CPC ...... *G09B 19/0092* (2013.01); *A23V 2002/00* (2013.01); *G01N 2405/00* (2013.01); *G01N 2405/04* (2013.01); *G01N 2570/00* (2013.01); *G01N 2800/324* (2013.01); *G01N 2800/50* (2013.01)

(56) References Cited

FOREIGN PATENT DOCUMENTS

| WO | WO/2004/085610 A2 | 10/2004 |
|---|---|---|
| WO | 2013113992 A1 | 8/2013 |
| WO | 2013139583 A1 | 9/2013 |
| WO | 2013186149 A1 | 12/2013 |
| WO | 2013186151 A1 | 12/2013 |

OTHER PUBLICATIONS

Balci, A., et al., Patients with psoriasis hav an increased amount of epicardial fat tissue, Clin. Exp. Dermatol., Mar. 2014; 39(2).
Graner, M., et al., Cardiac steatosis associates with visceral obesity in nondiabetic obese men, J. Clin. Endocrinol Metab., Mar. 2013; 98(3): 1189-1197.
Herzog, R., et al., A novel informatics concept for high-throughput shotgun lipidomics based on the molecular fragmentation query language, BioMed Central, Genome Biology, 2011.
Martin, R., et al., Cancer cachexia in the age of obesity: skeletal muscle depletion is a powerful prognostic factor, independent of body mass index, J. Clin. Oncol. Apr. 20, 2013;31(12):1539-47, Mar. 25, 2013.
Blachnio-Zabielska, AU, et al. Increased Bioactive Lipids Content in Human Subcutaneous and Epicardial Fat Tissue Correlates with Insulin Resistance. Lipids. Dec. 2012;47(12):1131-41.
Batra, A, and Siegmund, B. The role of visceral fat. Dig Dis. 2012;30(1):70-4.
Fu, CP, et al. Effects of weight loss on epicardial adipose tissue thickness and its relationship between serum soluble CD40 ligand levels in obese men. Clin Chim Acta. Jun. 5, 2013;421:98-103.
Cloarec, O, et al. Evaluation of the orthogonal projection on latent structure model limitations caused by chemical shift variability and improved visualization of biomarker changes in 1H NMR spectroscopic metabonomic studies. Anal Chem. Jan. 15, 2005;77(2):517-26.
Dogliotti. Glycerophospholipids profole in epicardial adipose tissue. Jan. 2012: pp. 1-75. Retrieved from the Internet on Mar. 19, 2014. <URL:http://air.unimi.it/bitstream/2434/168361/2/phd_unimi_R08007_2.pdf>.
Donahue, RP, and Abbott, RD. Central obesity and coronary heart disease in men. Lancet. Nov. 21, 1987;2(8569):1215.
Dulloo, AG, and Montani, JP. Phenotyping for early predictors of obesity and the metabolic syndrome. Int J Obes (Lond). Dec. 2010;34 Suppl 2:S1-3.
Fox, CS, et al. Abdominal visceral and subcutaneous adipose tissue compartments: association with metabolic risk factors in the Framingham Heart Study. Circulation. Jul. 3, 2007;116(1):39-48.
International Search Report for PCT/EP2014/077038, dated Jan. 30, 2015.
Kalkhoff, RK, et al. Relationship of body fat distribution to blood pressure, carbohydrate tolerance, and plasma lipids in healthy obese women. J Lab Clin Med. Oct. 1983;102(4):621-7.
Liaw, A, and Wiener, W. Classification and regression by randomForest. R News. 2002; 2/3:18-22.
Mahabadi, AA, et al. Association of epicardial fat with cardiovascular risk factors and incident myocardial infarction in the general population: the Heinz Nixdorf Recall Study. J Am Coll Cardiol. Apr. 2, 2013;61(13):1388-95.
Matyash, V, et al. Lipid extraction by methyl-tert-butyl ether for high-throughput lipidomics. J Lipid Res. May 2008;49(5):1137-46.
Pezeshkian, M, and Mahtabipour, MR. Epicardial and subcutaneous adipose tissue Fatty acids profiles in diabetic and non-diabetic patients candidate for coronary artery bypass graft. Bioimpacts. 2013;3(2):83-9.
Pezeshkian, M, et al. Influence of a High Cholesterol Regime on Epicardial and Subcutaneous Adipose Tissue Fatty Acids Profile in Rabbits. Metab Syndr Relat Disord. Oct. 2011;9(5):403-9.
Schuhmann, K, et al. Bottom-up shotgun lipidomics by higher energy collisional dissociation on LTQ Orbitrap mass spectrometers. Anal Chem. Jul. 15, 2011;83(14):5480-7.
Schuhmann, K, et al. Shotgun lipidomics on a LTQ Orbitrap mass spectrometer by successive switching between acquisition polarity modes. J Mass Spectrom. Jan. 2012;47(1):96-104.
Szymanska, E, et al. Gender-dependent associations of metabolite profiles and body fat distribution in a healthy population with central obesity: towards metabolomics diagnostics. OMICS. Dec. 2012;16(12):652-67.
Trygg, J, and Wold, S. O2-PLS, a two-block (X-Y) latent variable regression (LVR) method with an integral OSC filter. J Chemom. Jan. 2013; 17(1):53-64.
Wang, TD, et al. Relations of epicardial adipose tissue measured by multidetector computed tomography to components of the metabolic syndrome are region-specific and independent of anthropometric indexes and intraabdominal visceral fat. J Clin Endocrinol Metab. Feb. 2009;94(2):662-9.
Wold, S, Esbensen, K, and Geladi, P. Principal Component Analysis. Chemom Intell Lab Syst. 1987; 2:37-52.
Written Opinion of the International Searching Authority for PCT/EP2014/077038, dated Jan. 30, 2015.
Yamakado, M, et al. Plasma amino acid profile is associated with visceral fat accumulation in obese Japanese subjects. Clin Obes. Feb. 2012;2(1-2):29-40.
Chinese Patent Application for Invention No. 201480072250.4 Office Action dated Apr. 24, 2018 with Translation.

\* cited by examiner

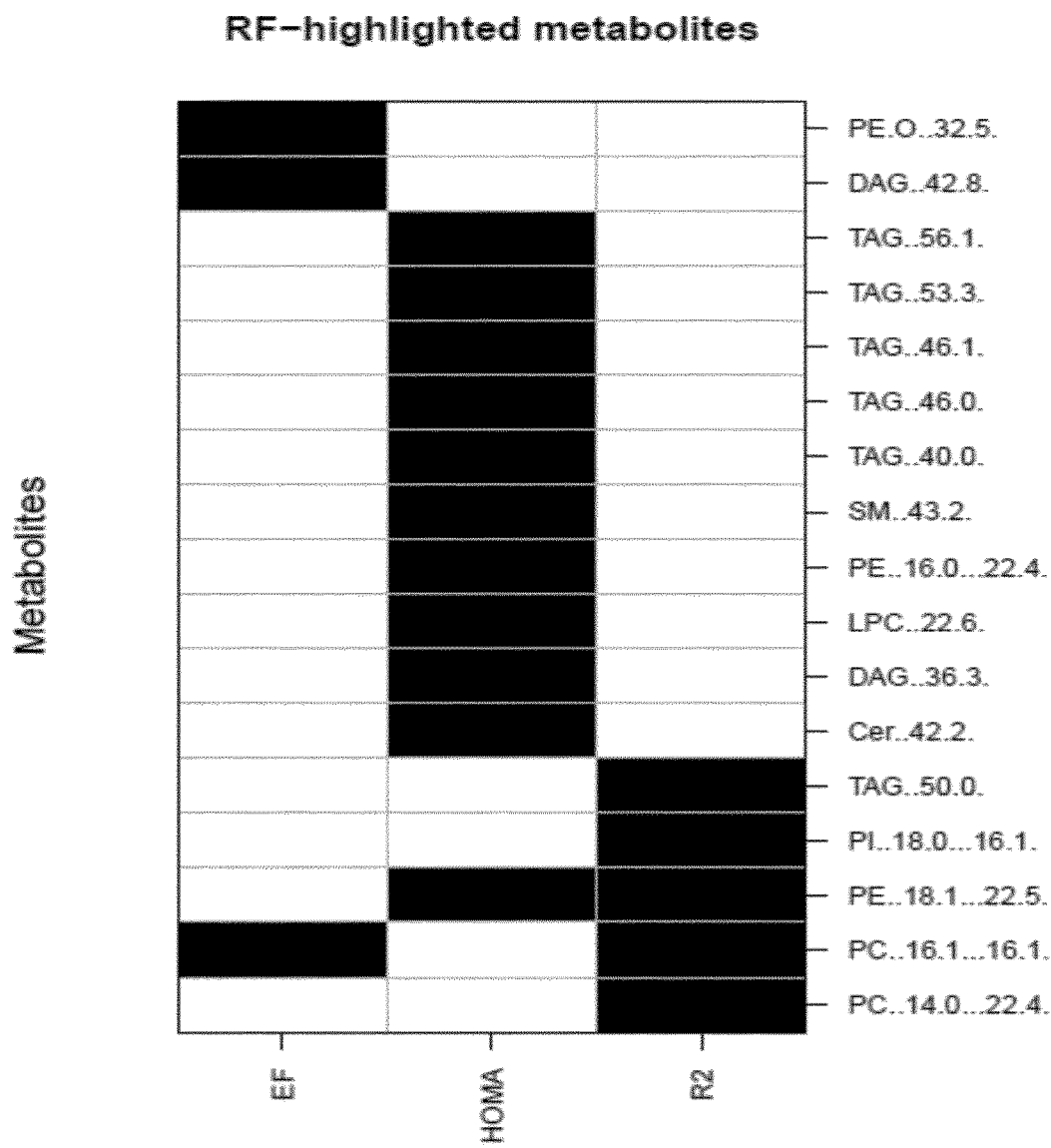

Summary of Relevant Variables for predicting Epicardial fat, Insulin resistance and Visceral adiposity. Legend: EF, Epicardial fat; HOMA, HOMA-IR; R2, Visceral adiposity. The table lists metabolite importance and robustness in predicting epicardial fat, visceral fat and HOMA-IR as assessed by Random forest analysis. Pooled mean decrease in accuracy after n=10000 random forest generations.

BIOMARKERS FOR EPICARDIAL ADIPOSE TISSUE

CROSS-REFERENCES TO RELATED APPLICATIONS

The present application is the National Stage of International Application No. PCT/EP2014/077038, filed on Dec. 9, 2014, which claims benefit to European Application No. 14150452.2, filed Jan. 8, 2014. The entire contents of the above applications are incorporated by reference as if recited in full herein.

FIELD OF THE INVENTION

The present invention provides a number of lipid biomarkers and biomarker combinations that can be used to predict levels of epicardial adipose tissue in a subject.

BACKGROUND

Visceral fat tissue is an important predictor of cardiometabolic disease, carrying more risk than general fat accumulation.

Metabolically deleterious and life threatening forms of obesity associate with accumulation of fat in the visceral adipose tissue and ectopic fat deposition in organs (Graner et al. (2013), 98: 1189-1197; Donahue and Abbott, (1987), Lancet 2: 1215; Kalkhoff et al. (1983), J Lab Clin Med 102: 621-627. In particular, higher visceral adiposity (VA) links to a higher probability of developing atherosclerotic cardiovascular diseases mediated via complex signaling metabolic functions that interplay with the endocrine and immune system (Batra and Siegmund, (2012), Dig Dis 30: 70-74; Fox et al. (2007), Circulation 116: 39-48).

Visceral fat includes a complex topographical fat deposition, namely mesenteric and epicardial adipose tissue, as well as peripheral depots around other organs (Dulloo et al. (2010), Int J Obes (Lond) 34 Suppl 2: S1-S3). The distinct metabolic differences existing between these visceral tissues result in specific contribution to disease etiologies.

Epicardial adipose tissue (EAT) is a particular form of visceral fat deposited around the heart. It is present on the surface of the heart between the myocardium and visceral pericardium and covers a significant surface of the heart.

An increase of the quantity of EAT is associated with incident coronary artery disease and with major adverse cardiac events (Mahabadi et al., 2013, J Am Coll Cardiol. 2013 Apr. 2; 61(13):1388-95) In particular, epicardial adipose tissue has a strong correlation with atherosclerosis, metabolic syndrome, impaired fasting glucose, insulin resistance, hypertension and diabetes mellitus.

Indeed, an increasing interest for general public health points towards childhood growth and obesity, where EAT is known as a major predictor for metabolic health.

It has also been shown that patients with psoriasis have a higher level epicardial fat compared with controls (Balci et al. 2013 Oct. 25, CED, 12216).

Epicardial adipose tissue can be measured by a number of imaging techniques including echocardiography, computer tomography (CT) and magnetic resonance imaging (MRI). However, such methods can be time consuming, expensive and are not appropriate for routine use.

Recent applications have demonstrated the feasibility of associating specific metabolite profiles to body fat distribution (Szymanska et al. (2012) OMICS 16: 652-667; Yamakado et al. (2012), Clinical Obesity 2: 29-40) including amino acids and various lipid species (triacylgylcerols, diacylglycerols, lysophospholipids, sphingomyelins, ceramides). However, markers associated with epicardial fat have not been identified.

Consequently, it was the objective of the present invention to provide lipid biomarkers that can be detected easily and that facilitate the prediction of EAT. Such lipid biomarkers can be used to promote healthy living by identifying subjects in need of reducing levels of EAT, and modifying the lifestyle of such subjects accordingly.

SUMMARY OF THE INVENTION

The present invention investigates the plasma lipidome and its encapsulated information with regards to specific visceral adipose depots. A shotgun lipidomics approach has been used to quantify blood plasma lipid profiles, and assess the composite metabolic signatures related to the specific body fat deposition, with emphasis on epicardial adipose tissue (EAT).

Accordingly the present invention provides in one aspect a method for predicting levels of EAT in a subject comprising:
(a) determining a level of one or more lipid biomarkers in a sample from the subject, wherein the biomarkers are selected from the following:
(i) phosphatidylcholine (PC) [16:1/16:1]
(ii) diacylglycerol (DAG) [42:8]
(iii) phosphatidylethanolamine-ether (PE-O) [32:5]
(iv) phosphatidylcholine (PC) [18:0/22:5]
(v) phosphatidylinositol (PI) [18:0/16:1]
(vi) phosphatidylglycerol (PG) [20:3/20:3]
(vii) phosphatidylglycerol (PG) [22:5/18:1]
(b) comparing the levels of the biomarkers in the sample to reference values;
wherein the levels of the biomarkers in the sample compared to the reference values are indicative of levels of EAT in the subject.

According to the present invention there is also provided a method for predicting levels of epicardial adipose tissue (EAT) in a subject comprising:
(a) determining a level of one or more lipid biomarkers in a sample from the subject using a detection device, wherein the biomarkers are selected from the following:
(i) phosphatidylcholine (PC) [16:1/16:1]
(ii) diacylglycerol (DAG) [42:8]
(iii) phosphatidylethanolamine-ether (PE-O) [32:5]
(iv) phosphatidylcholine (PC) [18:0/22:5]
(v) phosphatidylinositol (PI) [18:0/16:1]
(vi) phosphatidylglycerol (PG) [20:3/20:3]
(vii) phosphatidylglycerol (PG) [22:5/18:1]
and predicting the level of EAT in the subject based on the levels of the biomarkers in the sample relative to the reference values.

Preferably the detection device is a mass spectrometer.

Preferably, the method comprises determining a level of one or more lipid biomarkers selected from PC [16:1/16:1], DAG [42:8] and PE-O [32:5] in the sample from said subject.

In one embodiment, the method comprises determining a level of two or more lipid biomarkers selected from PC [16:1/16:1], DAG [42:8] and PE-O [32:5] in the sample from said subject.

In another embodiment, the method comprises determining a level of each of PC [16:1/16:1], DAG [42:8] and PE-O [32:5] in the sample from said subject.

In one embodiment, a level of PC [16:1/16:1] is determined, and a decrease in the level of PC [16:1/16:1] in the sample from the subject compared to the reference sample is indicative of higher levels of EAT.

In another embodiment, a level of DAG [42:8] is determined, and an increase in the level of DAG [42:8] in the sample from the subject compared to the reference sample is indicative of higher levels of EAT.

In another embodiment a level of PE-O [32:5] is determined, and an increase in the level of PE-O [32:5] in the sample from the subject compared to the reference sample is indicative of higher levels of EAT.

In another embodiment a level of PC [18:0/22:5] is determined, and an increase in the level of PC [18:0/22:5] in the sample from the subject compared to the reference sample is indicative of higher levels of EAT.

In another embodiment a level of PI [18:0/16:1] is determined, and an increase in the level of PI [18:0/16:1] in the sample from the subject compared to the reference sample is indicative of higher levels of EAT.

In another embodiment a level of PG [20:3/20:3] is determined, and an increase in the level of PG [20:3/20:3] in the sample from the subject compared to the reference sample is indicative of higher levels of EAT.

In another embodiment a level of PG [22:5/18:1] is determined, and an increase in the level of PG [22:5/18:1] in the sample from the subject compared to the reference sample is indicative of higher levels of EAT.

In another embodiment the method comprises determining a level of two, three, four, five, six, or all of the following lipid biomarkers in a sample from the subject: PC [16:1/16:1], DAG [42:8], PE-O [32:5], P) [18:0/22:5], PI [18:0/16:1], PG [20:3/20:3] and PG [22:5/18:1].

In one embodiment, the sample comprises serum or plasma obtained from the subject.

In another embodiment, the reference value is based on a mean level of the biomarker in a control population of subjects.

In another embodiment, the levels of the biomarkers are determined by lipidomic analysis.

The majority of the platforms for lipidomic analysis currently used are based on electrospray ionization (ESI) in conjunction with tandem mass spectrometry (MS/MS) analyses. The approaches based on ESI-MS can be classified into two categories that depend on whether liquid chromatography (LC) is performed prior to infusion into the mass spectrometer.

Liquid chromatography-mass spectrometry (LC-MS), or alternatively HPLC-MS is an analytical chemistry technique that combines the physical separation capabilities of liquid chromatography (or HPLC) with the mass analysis capabilities of mass spectrometry (MS).

Approaches in which direct infusion of samples (e.g., organic extracts) into the ion source is used are broadly termed Shotgun Lipidomics.

Shotgun Lipidomics uses direct infusion to avoid difficulties from alterations in concentration, chromatographic anomalies, and ion-pairing alterations.

In another embodiment, the levels of the biomarkers are determined by an untargeted shotgun lipidomic analysis.

Shotgun analysis provides a rapid quantitative snapshot of the molecular composition of a given biological matrix. Typically, lipids are extracted from cells, body fluids or tissues and directly infused into a mass spectrometer, completely bypassing the necessity of chromatographic pre-separation. A combination of over 100,000 mass resolution and sub-ppm mass accuracy of hybrid Orbitrap instruments enables the identification and quantification of lipid species from MS survey spectra and their respective MS/MS spectra.

The main advantages of this approach compared to conventional targeted analysis by triple-quadrupole MS are the untargeted, fast and reliable identification and quantification of individual lipid species from various lipid classes without any constraints applied on the molecular composition.

In one embodiment, the levels of the biomarkers in the sample compared to the reference values are indicative of the risk of developing diseases associated with raised levels of EAT, such as cardiovascular or metabolic disorders.

In another embodiment, the levels of the biomarkers in the sample compared to the reference values are indicative of the risk of developing diseases associates with raised levels of EAT such as atherosclerosis, coronary heart disease, metabolic syndrome impaired fasting glucose, insulin resistance, hypertension and diabetes mellitus.

In another embodiment, the levels of the biomarkers in the sample compared to the reference values are indicative of developing a cardiovascular disorder or metabolic disorder.

In another embodiment, the levels of the biomarkers in the sample compared to the reference values are indicative of developing atherosclerosis, coronary heart disease, metabolic syndrome, impaired fasting glucose, insulin resistance, hypertension and diabetes mellitus.

In another embodiment, the levels of the biomarkers in the sample compared to the reference values are indicative of the risk of losing cardioprotective effects associated with reduced levels of EAT in healthy subjects or restoring cardioprotective effects in unhealthy subjects who had too much EAT.

In a further aspect of the present invention there is provided a method for modulating the levels of epicardial adipose tissue (EAT) in a subject, comprising modifying a lifestyle of the subject to modulate the level of EAT if the subject has previously been identified as having levels of the biomarkers which are indicative of an unhealthy level of EAT using the methods described above.

In a further aspect, the present invention provides a method for modulating the level of EAT in a subject, comprising:
(a) determining the levels of the biomarkers using the methods described above,
(b) modifying a lifestyle of the subject to modulate the level of EAT if the subject has levels of the biomarkers which are indicative of an unhealthy level of EAT.

In a further aspect, the present invention provides a method for selecting a modification of lifestyle of a subject in order to modulate the level of epicardial adipose tissue (EAT) in said subject, the method comprising:
(a) determining the levels of the biomarkers using the methods described above,
(b) selecting a suitable modification in lifestyle based upon the level of biomarkers determined in step (a).

Preferable, 'modulating the level of EAT' or 'modulate the level of EAT' involves reducing or preventing an increase in EAT.

In one embodiment, the modification in lifestyle in the subject comprises a change in diet. Preferably the change in diet comprises administering at least one nutritional product to the subject that is part of a diet that modulates levels of EAT e.g., promotes a reduction in EAT or prevents an increase in EAT.

For example, the change in diet may comprise a decreased consumption of fat and/or an increase in consumption of low fat foods.

By way of example only, low fat foods may include wholemeal flour and bread, porridge oats, high-fibre breakfast cereals, wholegrain rice and pasta, vegetables and fruit, dried beans and lentils, baked potatoes, dried fruit, walnuts, white fish, herring, mackerel, sardines, kippers, pilchards, salmon and lean white meat In one embodiment, the method comprises a further step of repeating the step of predicting levels of EAT in a subject after modifying the lifestyle of the subject.

Accordingly to another aspect of the present invention there is provided a method for predicting the risk of developing a cardiovascular or metabolic disorder in a subject comprising:
(a) determining a level of one or more lipid biomarkers in a sample from the subject, wherein the biomarkers are selected from the following:
(i) phosphatidylcholine (PC) [16:1/16:1]
(ii) diacylglycerol (DAG) [42:8]
(iii) phosphatidylethanolamine-ether (PE-O) [32:5]
(iv) phosphatidylcholine (PC) [18:0/22:5]
(v) phosphatidylinositol (PI) [18:0/16:1]
(vi) phosphatidylglycerol (PG) [20:3/20:3]
(vii) phosphatidylglycerol (PG) [22:5/18:1]
(b) comparing the levels of the biomarkers in the sample to reference values;
wherein the levels of the biomarkers in the sample compared to the reference values are indicative of the risk of developing the metabolic or cardiovascular disorder.

In one embodiment, the cardiovascular disorder is atherosclerosis or coronary heart disease.

In another embodiment, the metabolic disorder is impaired fasting glucose, insulin resistance or diabetes mellitus.

DESCRIPTION OF FIGURES

FIG. 1 is a summary of relevant variables for predicting epicardial fat, Insulin resistance and Visceral adiposity. Legend: EF, Epicardial fat; HOMA, HOMA-IR; R2, Visceral adiposity. The table lists metabolite importance and robustness in predicting epicardial fat, visceral fat and HOMA-IR as assessed by Random forest analysis. Pooled mean decrease in accuracy after n=10000 random forest generations.

DETAILED DESCRIPTION OF THE INVENTION

Predicting Levels of EAT in a Subject

The present invention relates in one aspect to a method of predicting a level of epicardial adipose tissue (EAT) in a subject. In particular embodiments, the method may be used to diagnose unhealthy levels of EAT, to monitor the levels of EAT over a period of time or to identify subjects at risk of diseases associated with EAT.

For instance, the method may be used to predict the likelihood of a subject having or acquiring a disease associated with EAT, or to assess the current levels of EAT in the subject. The method may also be used to assess the efficacy of an intervention to promote modulations, in particular reductions, in EAT levels. For instance, the present invention may be used to monitor the effectiveness of a lifestyle change or change in diet.

Typical diseases associated with elevated EAT levels are known to those of skill in the art but include cardiovascular and metabolic disorders.

Typical EAT related disorders include atherosclerosis, coronary heart disease, metabolic syndrome, impaired fasting glucose, insulin resistance, hypertension and diabetes mellitus.

Subject

The present method may be carried out on any subject, including non-human or human subjects. In one embodiment, the subject is a mammal, preferably a human. The subject may alternatively be a non-human mammal, including for example a horse, cow, sheep or pig. In one embodiment, the subject is a companion animal such as a dog or cat.

Sample

The present method comprises a step of determining the level of one or more lipid biomarkers in a sample obtained from a subject. Thus the present method is typically practiced outside of the human or animal body, e.g. on a body fluid sample that was previously obtained from the subject to be tested. Preferably the sample is derived from blood, i.e. the sample comprises whole blood or a blood fraction. Most preferably the sample comprises blood plasma or serum.

Techniques for collecting blood samples and separating blood fractions are well known in the art. For instance, vena blood samples can be collected from patients using a needle and deposited into plastic tubes. The collection tubes may, for example, contain spray-coated silica and a polymer gel for serum separation. Serum can be separated by centrifugation at 1300 RCF for 10 min at room temperature and stored in small plastic tubes at −80° C.

Determining Levels of Lipid Biomarkers in the Sample

The levels of individual lipid species in the sample may be measured or determined by any suitable method. For example, mass spectroscopy (MS) may be used. Other spectroscopic methods, chromatographic methods, labeling techniques, or quantitative chemical methods may be used in alternative embodiments. Most preferably, the lipid levels in the sample are measured by mass spectroscopy, in particular shotgun mass spectroscopy. Typically the lipid level in the sample and the reference value are determined using the same analytical method.

Lipids

The present method involves determining the levels of lipid biomarkers selected from phosphatidylcholines (PCs), diacylglycerols (DAGs), Phosphatidylethanolamine-ethers (PE-Os), phosphatidylinositols (PIs) and phosphatidylglycerol (PGs).

The method involves measuring levels of at least one biomarker. By combining measurements of biomarkers an improved lipid biomarker signature of EAT may be achieved.

Phosphatidylcholines

In one embodiment, the level of a phosphatidylcholine (PC) having the structure PC [16:1/16:1] and/or PC [18:0/22:5] is determined. In the nomenclature (X:Y), X refers to the total number of carbon atoms in the fatty acid portions of the molecule, and Y defines the total number of double bonds in the fatty acid portions of the molecule. The nomenclature (X1:Y1/X2:Y2) refers to the number of carbon atoms (X) and double bonds (Y) in the first (1) and second (2) fatty acid chain of the PC species. Thus PC (18:0/22:5) comprises 18 carbon atoms and no double bonds in a first fatty acid chain, and 22 carbon atoms and 5 double bonds in a second fatty acid chain.

Diacylglycerols

In one embodiment, the level of a diacylglycerol (DAG) having the structure [42:8] is determined (using the nomenclature (X:Y) as defined above.

Phosphatidylethanolamine-Ethers

In one embodiment, the level of a phosphatidylethanolamine-ether (PE-0) having the structure [32:5] is determined (using the nomenclature (X:Y) as defined above).

Phosphatidylinositols

In one embodiment, the level of a phosphatidylinositol (PI) having the structure [18:0/16:1] is determined (using the nomenclature (X:Y) as defined above).

Phosphatidylglycerols

In one embodiment, the level of a Phosphatidylglycerol (PG) having the structure [20:3/20:3] and/or [22:5/18:1] is determined (using the nomenclature (X:Y) as defined above).

Combinations of Biomarkers

Whilst individual lipid biomarkers may have predictive value in the methods of the present invention, the quality and/or the predictive power of the methods may be improved by combining values from multiple lipid biomarkers.

Thus the method of the present invention may involve determining the level of at least two lipid biomarkers from those defined above. For instance, the method may comprise determining levels of 2, 3, 4, 5 6 or 7 of lipid species as described above.

A method comprising detecting the combination including PC [16:1/16:1], DAG [42:8] and PE-O [32:5] is particularly preferred.

Comparison to Control

The present method further comprises a step of comparing the level of the individual lipid species in the test sample to one or more reference or control values. Typically a specific reference value for each individual lipid species determined in the method is used. The reference value may be a normal level of that lipid species, e.g. a level of the lipid in the same sample type (e.g. serum or plasma) in a normal subject. The reference value may, for example, be based on a mean or median level of the lipid species in a control population of subjects, e.g. 5, 10, 100, 1000 or more normal subjects (who may either be age- and/or gender-matched or unmatched to the test subject).

The extent of the difference between the subject's lipid biomarker levels and the corresponding reference values is also useful for determining which subjects would benefit most from certain interventions. The level of the lipid in the test sample may be increased or decreased by, for example, at least 1%, 5%, at least 10%, at least 20%, at least 30%, at least 50% or at least 100% compared to the reference value.

In some embodiments, the reference value is a value obtained previously from the same subject. This allows a direct comparison of the effects of a current lifestyle of the subject compared to a previous lifestyle on lipid biomarker levels associated with EAT, so that improvements can be directly assessed.

The reference value may be determined using corresponding methods to the determination of lipid levels in the test sample, e.g. using one or more samples taken from normal subjects. For instance, in some embodiments lipid levels in control samples may be determined in parallel assays to the test samples. Alternatively, in some embodiments reference values for the levels of individual lipid species in a particular sample type (e.g. serum or plasma) may already be available, for instance from published studies. Thus in some embodiments, the reference value may have been previously determined, or may be calculated or extrapolated, without having to perform a corresponding determination on a control sample with respect to each test sample obtained.

Association of Lipid Levels to EAT

In general, an increased or decreased level of the above lipid species in the test sample compared to the reference value may be indicative of higher or lower levels of EAT. The overall level of EAT and/or the risks of disease associated with EAT may be assessed by determining the levels of different lipid biomarkers as discussed above. For instance, subjects may be stratified into low, medium, high and/or very high prediction of EAT level according to the number of individual lipid species which are modulated relative to control and/or the degree to which they are elevated.

Alternatively, subjects may be stratified into low, medium, high and/or very high risk groups for diseases associated with EAT according to the number of individual lipid species which are modulated relative to control and/or the degree to which they are elevated.

Methods for Promoting Healthy Levels of EAT

In one aspect, the present invention provides a method for modulating the levels of EAT in a subject. In particular, the method may be used to reduce the risk of EAT related conditions or diseases in the subject, or to improve longevity in the subject.

The method comprises a first step of determining a likelihood of unhealthy levels of EAT in the subject by a method as described above. Following the determination of the likelihood of unhealthy levels of EAT in the subject, an appropriate intervention strategy (e.g. a change in lifestyle and/or diet) may be selected for the subject, based on assessed risk level.

Typically if the subject is predicted to have low levels of EAT, no intervention may be necessary. For instance, if the subject's predicted level of EAT is at or below a threshold level, no pharmaceutical or nutritional therapy may be required. The threshold level may correspond, for example, to a normal or mean level of EAT in the general population.

Alternatively, if the subject is predicted to have elevated levels of EAT, the method may comprise a further step of modifying a lifestyle of the subject. The modification in lifestyle in the subject may be any change as described herein, e.g. a change in diet, more sports, a different working and/or living environment etc.

Preferably the change is the use of at least one nutritional product that was previously not consumed or consumed in different amounts, e.g. a nutritional product that has an effect on levels of EAT and/or has an effect on avoiding EAT related disorders (including food products, drinks, pet food products, food supplements, nutraceuticals, food additives or nutritional formulas). In particularly preferred embodiments, the change in diet comprises a decreased level of fat.

Modifying a lifestyle of the subject also includes indicating a need for the subject to change his/her lifestyle, e.g. prescribing, promoting and/or proposing a lifestyle change as described above to the subject. For instance, the method may comprise a step of administering or providing at least one nutritional product as described above to the subject.

A lifestyle modification can be selected which is effective in modulating levels of the specific lipid species associated with EAT. Typically, different lifestyle modifications (e.g. individual nutritional products) may have differing effects on the profiles of individual lipid species in individual subjects, due to various factors such as genetic variability and environment.

The lifestyle modification may be personalized to the subject, such that lipid levels are monitored in conjunction with a specific program targeted to modulate those individual lipid species in the subject. For instance, the method may comprise a further step of (re-)determining lipid levels in the subject (i.e. after the initial lifestyle or diet-based intervention), in order to assess the effectiveness of the therapy. For example, if the subject shows a reduction in EAT levels after the initial intervention phase, the intervention may be continued to maintain the reduction.

However, if the subject fails to respond adequately to the initial intervention (e.g. shows no significant change in specific lipid levels), the subject may be switched to an alternative program, e.g. a different lifestyle modification, diet or nutritional agent. For example, if a subject responds poorly to an initial nutritional regime, an alternative nutritional product may be administered to the subject. This process may be repeated, including selecting different dosages of individual agents, until a desired change in EAT levels is achieved. Typically, the subject may be maintained on a particular regime (e.g. a nutritional agent such as those defined above) for at least 1 week, 2 weeks, 1 month or 3 months before the determination of lipid levels is repeated.

The method may be used to monitor the effects of lifestyle changes (such as changes in diet, exercise levels, smoking, alcohol consumption and so on) on EAT associated lipid levels, and to identify a combination of factors which is effective in modulating levels of EAT.

In a further aspect, the present invention provides a nutritional agent as defined above (e.g. selected from food products, drinks, pet food products, food, nutraceuticals, food additives or nutritional formulas), for use in modulating levels of EAT (or preventing or treating diseases associated with EAT) in a subject, wherein an unhealthy level of EAT in the subject has been predicted by a method as described above.

In a further aspect, the present invention provides use of a nutritional agent as defined above, for the manufacture of a medicament for modulating levels of EAT (or preventing or treating diseases associated with EAT) in a subject, wherein an unhealthy level of EAT in the subject has been predicted by a method as described above.

Kits

In a further aspect, the present invention provides a kit for predicting the level of EAT in a subject. The kit may, for example, comprise one or more reagents, standards and/or control samples for use in the methods described herein. For instance, in one embodiment the kit comprises one or more reference samples comprising predetermined levels of (i) PC [16:1/16:1], (ii) DAG [42:8], (iii) PE-O [32:5], (iv) PC [18:0/22:5], (v) PI [18:0/16:1], (vi) PG [20:3/20:3] and/or (vii) PG [22:5/18:1], and instructions for use of the kit for predicting EAT in a subject by comparing the predetermined levels in the reference sample to levels of lipids in a sample obtained from the subject.

Those skilled in the art will understand that they can freely combine all features of the present invention described herein, without departing from the scope of the invention as disclosed. The invention will now be described by way of example only with respect to the following specific embodiments.

EXAMPLES

Example 1—Materials and Methods

Participants and Experimental Design

The observational study was conducted on 40 healthy obese Caucasian women at the out-patient obesity clinic of the University Hospital of Lausanne (CHUV), Switzerland, after receiving informed consent from the appropriate ethical review board at CHUV. The participants had a BMI between 28 and 40, aged between 25 and 45 years old and showed no metabolic disease traits. Additional exclusion criteria were diabetes, pregnancy, antibiotic therapy within 1 month prior to the beginning of the study, any therapy (contraception apart) within the run-in period of one week before the visit day, and eating disorders. Subjects having recently undergone a weight loss of more than 3 kilos during the last 3 months were also excluded. No subjects suffered from hypertension, glucose intolerance, polycystic ovary syndrome, thyroid dysfunction and adrenal disorders. At a baseline (V0), subjects underwent a standard medical visit, where overnight fasting blood plasma samples were collected. One week later (V1), body composition was measured using CT (at CHUV) and iDXA (at the metabolic unit, Nestlé Research Center, Lausanne, Switzerland), resting energy expenditure was measured by indirect calorimetry and a standard Oral Glucose Tolerance Test (OGTT, 75 g glucose) was conducted. One week later (V2), overnight fasting plasma and 24-hours urine samples were collected and subjected to metabonomic and lipidomic analysis.

Chemicals and Standards

Ethanol, chloroform and iso-propanol (HPLC grade) were purchased from Biosolve (Valkenswaard, the Netherlands). Methanol, water and ammonium acetate were obtained from Merck (Darmstadt, Germany). Synthetic lipid standards were purchased from Avanti Polar Lipids with purities higher than 99%. Stock-solutions of individual lipid compounds were prepared in methanol and stored at −20° C. Working solutions of the desired concentrations were prepared by dilution in isopropanol/methanol/chloroform 4:2:1 (v/v/v).

Clinical, Anthropometric and Body Composition Measurements

These parameters were measured as previously reported (Martin et al. (2013)). Briefly, clinical and anthropometric measures (body weight, height, waist, hip) were conducted using standard clinical practices. Full body scan was performed to determine both abdominal fat distribution and total body composition. Total body scans were made on a GE Lunar iDXA system (software version: enCORE version 12.10.113) with scan mode automatically determined by the device and used the previously reported procedure (Martin et al. (2013)).

The CT scan measures of the abdominal region, for the quantification of intra-peritoneal and sub-cutaneous fat, were performed on 64 multi-detector CT scanner (VCT Lightspeed, GE Medical Systems, Milwaukee, USA), as described previously (Martin et al. (2013)). Subjects lay in the supine position with their arms above their head and legs elevated with a cushion. A single scan (10 mm) of the abdomen is acquired at the level of L4-L5 vertebrae and analyzed for a cross-sectional area of adipose tissue, expressed in square centimeters. The following acquisition parameters were used: 120 Kv, 100-200 mA with z-axis dose modulation and a field of view 500 mm. Axial transverse images of 5 mm slice thickness are reconstructed using a standard kernel. The quantification process uses a semi interactive commercially available algorithm for segmentation of subcutaneous and intra-abdominal fat on the Advantage Window workstation (GE Medical Systems). Resting metabolic rate was measured by using open-circuit indirect calorimetry, with a Deltatrak II (Datex Instruments).

The further CT scan measures of the intrapericardic, extrapericardic and mediastinal fat were performed High resolution cardiac fat deposition was generated from 28 out of the 40 subjects.

Shotgun Lipidomics Analysis

A high throughput, fully automated liquid/liquid extraction method utilizing a Hamilton Microlabstar robot (Hamilton, Bonaduz, Switzerland) was developed in house for lipidomics extraction with minor modifications from previous methods (Matyash et al., (2008) J Lipid Res 49: 1137-1146). 96 samples were extracted in less than 3 hours. Briefly, 5 µL of serum was used for sample clean-up. Lipid extraction was performed with 700 µL MTBE/MeOH (10/3) containing an internal standard mixture of 5 µM TAG 44:1, 0.5 µM DAG 24:0, 5 µM PC 28:0, 1 µM LPC 14:0, 1 µM PE 28:0, 0.5 µM LPE 14:0, 1 µM PS 28:0, 0.5 µM LPS 17:1, 1 µM PI 32:0, 0.5 µM LPI 17:1, 0.5 µM PA 28:0, 0.5 µM LPA 14:0, 1 µM PG 28:0, 0.5 µM LPG 14:0, 2 µM SM 35:1, 1 µM Cer 32:1. Samples were vortexed at 4° C. for 1 hour, followed by the addition of 150 µL water to induce phase separation. After centrifugation for 10 min at 5,000 g, 500 µL of the upper organic phase was transferred into a 96-deepwell-plate (Eppendorf, Hamburg, Germany), sealed with aluminum foil and stored at −20° C. until analysis. Prior to MS analysis 10 µL of total lipid extract were finally diluted with 90 µL of MS running buffer (isopropanol/methanol/chloroform 4:2:1 (v/v/v) containing 7.5 mM ammonium acetate.

A shotgun lipidomics approach was developed in house based on previously published work (Schuhmann et al., (2012) J Mass Spectrom 47: 96-104, and Schuhmann et al. (2011) Anal Chem 83: 5480-5487) Analysis was carried out on an LTQ Orbitrap Velos MS (Thermo Fisher Scientific, Reinach, Switzerland) system coupled to a Nanomate nanoinfusion ion source (Advion Bioscience Ltd, Harlow, Essex, UK). For each sample extract, two consecutive injections were performed for negative and positive ionization mode, respectively. Centroided high collisional dissociation (HCD) negative MS/MS were acquired in DDA mode. Each DDA cycle consisted of one MS survey spectra acquired at the target resolution $R_{m/z400}$ of 100,000, followed by the acquisition of 20 HCD FT MS/MS spectra at the resolution $R_{m/z400}$ of 30,000. One DDA experiment was completed in 25 min. Precursor ions were subjected to MS/MS only if their m/z matched the masses of a precompiled inclusion list with an accuracy of 5 ppm. In positive ionization mode MS spectra were acquired at the target resolution $R_{m/z400}$ of 100,000, no further MS/MS experiments were performed. The lock mass option was enabled using LPA 17:0 (m/z 424.492; negative mode) and d18:1/17:0 Cer (m/z 551.528; positive mode) as reference peaks.

Lipid species were identified by LipidXplorer following the protocol of Herzog and co-workers (Herzog et al. (2011), Genome Biol 12: R8). Data were then exported and further processed by an in-house developed software tool. The routine merged the data sets and generated Excel-output-files containing the normalized values (Internal standard to analyte ratio) and absolute concentrations by comparing the abundances of precursor ions of analyte and internal standard spiked prior to extraction.

Lipids have been annotated according to Lipid Maps classification and nomenclature system (http://www.lipidmaps.org): PC, Phosphatidylcholine; PC-O, Phsophatidylcholine-ether; LPC, Lysophosphatidylcholine; PE, Phosphatidylethanolamine; PE-O, Phsophatidylethanolamine-ether; LPE, Lysophosphatidylethanolamine; PS, Phosphatidylserine; LPS, Lysophosphatidylserine; PI, Phosphatidylinositol; LPI, Lysophosphatidylinositol; PG, Phosphatidylglycerol; Cer, Ceramide; SM, Sphingomyelin; DAG, Diacylglycerol; TAG, Triacylglycerol, Phosphatidic acid; PA. In general, individual lipid species were annotated as follows: [lipid class] [total number of carbon atoms]:[total number of double bonds].

Chemometrics

Chemometric analysis was performed using the software package SIMCA-P+ (version 13.0, Umetrics AB, Umeå, Sweden) and in-house developed MATLAB (The Math-Works Inc., Natick, Mass., USA) routines. Principal Component Analysis (PCA) (Wold S, Esbensen K, Geladi P (1987) Principal Component Analysis. Chemom Intell Lab Syst 2: 37-52), Projection to Latent Structure (PLS) (Wold S, Hellberg S, Lundstedt T, Sjostrom M (1987) PLS Modeling with Latent Variables in Two or More Dimensions. PLS Meeting, Frankfurt), and the Orthogonal Projection to Latent Structures (O-PLS) (Trygg J, Wold S (2003) J Chemom 17: 53-64) were used to investigate relationships between epicardial and visceral fat and lipidomic profiles. Seven-fold cross validation was used to assess the validity of the models (Cloarec et al. (2005), Anal Chem 77: 517-526).

In addition, Lipidomics data were analyzed by Random Forests using the package 'randomForest' (RF™) (Liaw et al., 2002, R News 3: 18-22) (with 500 trees, and a random variable sampling at tree split of 5) and using the variable importance features implemented in RF™ (mean decreases in accuracy/node impurity) to determine variables that associate better with visceral and epicardial fat status as assessed using either value of the absolute or body fat ratios.

Spearman autocorrelation matrices were calculated using the statistical computing software environment R and corresponding graphs were produced using the package Rgraphviz v.1.32.0. Univariate significance tests for validation were also performed in R.

Example 2

The plasma lipidome and its encapsulated information with regards to specific visceral adipose depots was investigated. In particular, modern imaging technologies based on magnetic resonance (MRI) and CT can generate accurate regio-specific quantification of visceral fat depots, including EAT (Wang et al. (2009) J Clin Endocrinol Metab 94: 662-669). Within the same cohort study of healthy obese women, a shotgun lipidomics approach was applied to quantify blood plasma lipid profiles, and assess the composite metabolic signatures related to the specific body fat deposition, with emphasis on VA, EAT and insulin resistance. The present study therefore provides complementary and novel insights on how the topography of visceral adiposity links differently to the blood plasma lipidome of healthy obese women.

Relationships Between Epicardial Fat Measures, Clinical and Body Composition Parameters Anthropometric and clinical data for the cohorts are reported in tables 1 and 2. Initial PCA and spearman correlation analysis showed that intrapericardic fat, mediastinal fat, and epicardiac fat parameters correlate strongly with other visceral fat estimates, (e.g. $Log_{10}$ values of intraperitoneal fat (IPVF) (r=0.56, p=0.002; r=0.65, p<0.001; r=0.66, p<0.001), VAT/SAT (r=0.49, p=0.008; r=0.50, p=0.006; r=0.40, p=0.031) and VAT/total abdominal fat ratios (r=0.49, p=0.008; r=0.49, p=0.006; r=0.39, p=0.037), BMI (r=0.45, p=0.016; r=0.54, p=0.003; r=0.60, p<0.001), abdominal fat (r=0.39, p=0.040; r=0.51, p=0.005; r=0.56, p=0.002), subcutaneous fat (r=0.62, p<0.001; r=0.70, p<0.001; r=0.71, p<0.001), as well as total fat mass (r=0.44, p=0.019; r=0.52, p=0.004; r=0.55, p=0.002), but not with android/gynoid fat (FIG. 1). Moreover, mediastinal and intrapericardic fat correlates with several lean mass parameters. Similar to other visceral fat estimates, intrapericardic and mediastinal fat correlated strongly with ALAT (r=0.38, p=0.045; r=0.42, p=0.025), ALAT/ASAT ratio (r=0.49, p=0.007; r=0.56, p=0.002), blood triglycerides (r=0.48, p=0.009; r=0.45, p=0.016). Epicardial fat was mainly correlated to ALAT/ASAT ratio (r=0.47, p=0.011), whilst all the cardiac fat parameters strongly correlated with GGT (r=0.54, p=0.039; r=0.57, p=0.001; r=0.47, p=0.011). Interestingly, cardiac fat parameters were not statistically correlated with glucose and insulin parameters measured at fasting or during the OGTT, when compared to other visceral fat estimates. Ratios A and B were independent of most other parameters, except for positive correlations with BMI (r=0.41, p=0.028; r=0.41, p=0.028), epicardial fat (r=0.42, p=0.025; r=0.42, p=0.025) and negative correlations with region-specific bone mass distribution (e.g. for gynoid bone mass, r=−0.46, p=0.015 r=−0.46, p=0.015).

Epicardial, Visceral Adiposity and HOMA-IR Link to Specific Blood Plasma Lipid Composition Remodelling The blood plasma lipidome of the 40 subjects was characterized using validated shot gun lipidomic approach, for relative quantification of 252 lipid species over fourteen different classes. The analysis encompasses triacylglycerol TG (n=50), diacylglycerol DAG (n=18), sphingomyelin SM (n=24), ceramide Cer (n=17), phosphatidylinositol PI (n=12), lysophosphatidylinositol LPI (n=2), phosphatidyglycerol PG (n=6), phosphatidylethanolamine PE (n=23), ether phosphatidylethanolamine PE-O (n=15), lysophosphatidylethanolamine LPE (n=4), phosphatidylcholine PC (n=45), ether phosphatidylcholine PC-O (n=29), lysophosphatidylcholine LPC (n=6), and phosphatidic acid PA (n=1).

Using OPLS analysis, three models were generated using 1 predictive and 1 orthogonal component for visceral fat ($\log_{10}$ ratio of VAT/abdominal fat ratio, $R^2X$=0.16, $R^2Y$=0.87, $Q^2Y$=0.59), epicardiac fat ($R^2X$=0.32, $R^2Y$=0.81, $Q^2Y$=0.59, FIG. 2), and HOMA-IR ($R^2X$=0.32, $R^2Y$=0.55, $Q^2Y$=0.21).

Influential variables were investigated using Volcano plotting based on VIP and correlation coefficients values. In parallel, using the variable importance feature implemented in RF™, it was possible to determine the metabolic readouts that best associate with visceral fat, HOMA-IR and epicardial fat.

The metabolic signature of EAT is shown in Table 3. Moreover, Table 3 summarize the similarities and dissimilarities amongst influential variables with regards to VA, EAT and HOA-IR based on RF™ indexes.

The most discriminant variables were PC [16:1/16:1], DAG [42:8], PE-O [32:5]. Based on these analyses, we could define that PC [16:1/16:1], DAG [42:8], PE-O [32:5], PC [18:0/22:5], PI [18:0/16:1], PG [20:3/20:3] and PG [22:5/18:1]

TABLE 1

Descriptive body composition of subjects

| Factor | Mean ± SD (Min-Max) |
| --- | --- |
| Intrapericardic Fat volume (cm3) | 77.1 ± 33.0 (25.4-144.2) |
| Mediastinal total fat volume (cm3) | 136.0 ± 55.5 (44.6-231.7) |
| Mediastinal extra pericardic fat volume (epicardial fat, cm3) | 58.9 ± 26.1 (19.2-101.8) |
| Ratio Epicardic/total mediastinal | 0.4 ± 0.1 (0.3-0.7) |
| Ratio Epicardic/intrapericardic | 0.8 ± 0.3 (0.4-2.2) |
| Abdominal fat volume (mL) | 20123.4 ± 4443.7 (11338-33643) |
| Subcutaneous fat volume (mL) | 15733.5 ± 3571.4 (9263-25006) |

TABLE 1-continued

Descriptive body composition of subjects

| Factor | Mean ± SD (Min-Max) |
| --- | --- |
| Intraperitoneal fat volume (mL) | 4451.6 ± 1392.2 (2075-8637) |
| $\log_{10}$ IPVF | 3.6 ± 0.1 (3.3-3.9) |
| $\log_{10}$ Ratio 1 (VAT/SAT) | −0.7 ± 0.1 (−0.9--0.5) |
| $\log_{10}$ Ratio 2 (VAT/Abdominal Fat) | −0.6 ± 0.1 (−0.8--0.3) |
| Abdominal Vol | 34735.0 ± 5794.5 (24857-53498) |
| Abdominal Fat Vol | 20123.4 ± 4443.7 (11338-33643) |
| Sub-Cut Fat Vol | 6971.4 ± 4964.9 (2075-18511) |
| Android/Gynoid fat | 0.5 ± 0.1 (0.3-0.8) |
| Total fat mass | 44525.0 ± 8743.0 (31389.6-68339) |

Key: SAT = subcutaneous fat tissue VAT = visceral adipose tissue.

TABLE 2

Descriptive anthropometric and clinical parameters of subjects

| Factor | Mean ± SD (Min-Max) |
| --- | --- |
| Age (years) | 35.6 ± 5.1 (25-46) |
| BMI (kg/m²) | 35.5 ± 3.7 (29-43.7) |
| Hipp (cm) | 124.9 ± 7.6 (110-144) |
| Waist (cm) | 103.5 ± 11.0 (87.6-127.5) |
| Waist/Hipp ratio | 0.8 ± 0.1 (0.7-1) |
| Na (mmol/L) | 140.7 ± 1.4 (138-143) |
| K (mmol/L) | 4.0 ± 0.2 (3.5-4.4) |
| Glucose (mmol/L) | 5.2 ± 0.5 (4.3-6.3) |
| Creatinine (mmol/L) | 66.5 ± 9.2 (50-93) |
| Cholesterol (mmol/L) | 5.5 ± 0.9 (3.8-7) |
| HDL-C (mmol/L) | 1.4 ± 0.3 (0.9-2.6) |
| LDL-C (mmol/L) | 3.5 ± 0.8 (2.2-4.9) |
| TG (mmol/L) | 1.5 ± 1.2 (0.4-8) |
| Urates (µmol/L) | 282.2 ± 57.4 (172-421) |
| ASAT (U/L) | 22.8 ± 5.5 (13-40) |
| ALAT (U/L) | 22.1 ± 9.2 (10-56) |
| ALAT/ASAT ratio | 1.0 ± 0.3 (0.5-1.7) |
| MAP (mmHg) | 62.3 ± 18.6 (27-104) |
| GGT (U/L) | 20.9 ± 9.2 (9-47) |
| Calorimetry (Kcal/24 h) | 1423.3 ± 174.7 (1100-1970) |
| Insulin (µl/mL) | 22.6 ± 7.3 (0.6-39.8) |
| HOMA-IR | 5.3 ± 1.8 (0.1-9.6) |
| OGTT Insulin AUC | 315.4 ± 103.0 (111.6-521) |
| OGTT Glucose AUC | 450.9 ± 70.2 (333-617) |

Key: BMI = body mass index, HDL-C = high density lipoprotein cholesterol, homeostasis model assessment of insulin resistance = HOMA-IR, LDL-C = low density lipoprotein cholesterol, TG = triglycerides, MAP = mean arterial blood pressure, ALAT = alanine aminotransferase, ASAT = aspartate aminotransferase, GGT = gamma-glutamyl transpeptidase, OGTT = Oral glucose tolerance test.

TABLE 3

Metabolite importance and robustness in predicting EAT, VAT and HOMA-IR as assessed by Random forest analysis.

| EAT | HOMA-IR | VAT | LipidID |
| --- | --- | --- | --- |
| 3.172 | 0.32 | 4.646 | PC [16:1/16:1] |
| 2.677 | −0.024 | 0.69 | DAG [42:8] |
| 1.836 | −0.18 | −0.233 | PE-O [32:5] |
| 1.42 | 0.34 | −0.002 | PC [18:0/22:5] |
| 1.315 | 0.321 | 4.6 | PI [18:0/16:1] |
| 1.145 | 0.042 | −0.044 | PG [20:3/20:3] |
| 1.145 | 0.052 | −0.05 | PG [22:5/18:1] |
| 0.992 | −0.09 | 0.27 | Cer [41:2] |
| 0.869 | −0.268 | 1.961 | PC [14:0/20:3] |
| 0.562 | 0.184 | 2.147 | TAG [56:6] |
| 0.553 | 0.037 | 2.153 | TAG [56:7] |
| 0.547 | 0.047 | 0.623 | TAG [56:8] |
| 0.543 | 0.123 | 2.165 | TAG [50:4] |
| 0.542 | 0.163 | 2.169 | TAG [56:5] |
| 0.539 | 0.168 | 2.145 | TAG [51:2] |
| 0.534 | 0.128 | 2.139 | TAG [51:3] |
| 0.504 | −0.21 | 1.478 | PE-O [36:5] |

TABLE 3-continued

Metabolite importance and robustness in predicting EAT, VAT and HOMA-IR as assessed by Random forest analysis.

| EAT | HOMA-IR | VAT | LipidID |
|---|---|---|---|
| 0.237 | 0.902 | 0.099 | SM [43:2] |
| 0.227 | −0.113 | 1.923 | TAG [52:1] |
| 0.2 | −0.019 | 0.087 | PC-O [42:5] |
| 0.178 | −0.103 | 0.032 | PC-O [30:2] |
| 0.175 | 0.179 | 0.395 | LPI [16:0] |
| 0.163 | 0.123 | 0.201 | DAG [30:1] |
| 0.154 | 1.087 | 1.037 | TAG [53:3] |
| 0.141 | −0.058 | 1.048 | DAG [36:4] |
| 0.093 | 2.498 | 2.311 | PE [16:0/22:4] |
| 0.056 | −0.834 | 0.198 | PC-O [28:4] |
| 0.054 | −0.521 | 0.682 | LPC [20:3] |
| 0.041 | 0.381 | 0.304 | SM [40:3] |
| 0.01 | −0.08 | 1.395 | TAG [54:5] |
| 0 | 0 | 0 | PC [16:0/20:2] |
| −0.048 | 0.233 | 0.376 | PE [18:1/22:6] |
| −0.057 | 0.251 | 6.199 | PC [14:0/22:4] |
| −0.102 | 0.361 | 1.213 | TAG [48:4] |
| −0.128 | 0.867 | 0.737 | DAG [36:3] |
| −0.143 | 0.614 | 1.59 | TAG [54:1] |
| −0.171 | 0.346 | 1.687 | TAG [49:2] |
| −0.258 | 0.685 | 6.268 | PE [18:1/22:5] |
| −0.467 | −0.028 | −0.321 | LPE [16:0] |

Legend: Reported values corresponds to pooled mean decrease in accuracy after n = 10000 random forest generations. Higher variable importance corresponds to higher values of pooled mean decrease in accuracy.

The invention claimed is:

1. A method of promoting healthy levels of epicardial adipose tissue (EAT) in a subject, the method comprising:
    (a) determining a level of one or more lipid biomarkers in a sample from the subject, wherein the one or more lipid biomarkers are selected from the group consisting of:
        (i) phosphatidylcholine (PC) [16:1/16:1]
        (ii) diacylglycerol (DAG) [42:8]
        (iii) phosphatidylethanolamine-ether (PE-O) [32:5]
        (iv) phosphatidylcholine (PC) [18:0/22:5]
        (v) phosphatidylinositol (PI) [18:0/16:1]
        (vi) phosphatidylglycerol (PG) [20:3/20:3]
        (vii) phosphatidylglycerol (PG) [22:5/18:1]
    (b) determining a level of EAT in the subject by comparing the level of the one or more lipid biomarkers in the sample to reference values; and
    (c) modulating the level of EAT by providing a change in diet, the change in diet comprising administering to the subject one or more nutritional products effective to prevent an increase in the EAT of the subject and/or promote a reduction in the EAT of the subject when the determined level of EAT in step (b) is above a threshold level of EAT predetermined in a general population,
    wherein the one or more nutritional products comprise at least one low fat food product effective to prevent an increase in EAT and/or promote a reduction in the EAT of the subject, and
    the at least one low fat food product is selected from the group consisting of wholemeal flour and bread, porridge oats, high-fibre breakfast cereals, wholegrain rice and pasta, vegetables, fruit, dried beans, lentils, baked potatoes, dried fruit, walnuts, white fish, herring, mackerel, sardines, kippers, pilchards, salmon and lean white meat.

2. The method of claim 1, wherein the one or more lipid biomarkers for which the level is determined in step (a) are selected from the group consisting of:
    (i) PC [16:1/16:1]
    (ii) DAG [42:8]
    (iii) PE-O [32:5]
    in the sample from the subject.

3. The method of claim 1, wherein the one or more lipid biomarkers for which the level is determined in step (a) consist of at least two biomarkers selected from the group consisting of:
    (i) PC [16:1/16:1]
    (ii) DAG [42:8]
    (iii) PE-O [32:5]
    in the sample from the subject.

4. The method of claim 1, wherein the one or more lipid biomarkers for which the level is determined in step (a) consist of each of:
    (i) PC [16:1/16:1]
    (ii) DAG [42:8]
    (iii) PE-O [32:5]
    in the sample from the subject.

5. The method of claim 1 wherein a level of PC [16:1/16:1] is determined, and a decrease in the level of PC [16:1/16:1] in the sample from the subject compared to the reference value is indicative of higher levels of EAT.

6. The method of claim 1 wherein a level of DAG [42:8] is determined, and an increase in the level of DAG [42:8] in the sample from the subject compared to the reference value is indicative of higher levels of EAT.

7. The method of claim 1 wherein a level of PE-O [32:5] is determined, and an increase in the level of PE-O [32:5] in the sample from the subject compared to the reference value is indicative of higher levels of EAT.

8. The method of claim 1 wherein:
    a level of PC [18:0/22:5] is determined, and an increase in the level of PC [18:0/22:5] in the sample from the subject compared to the reference value is indicative of higher levels of EAT, and/or
    a level of PC [20:3/20:3] is determined, and an increase in the level of PC [20:3/20:3] in the sample from the subject compared to the reference value is indicative of higher levels of EAT, and/or
    a level of PG [22:5/18:1] is determined, and an increase in the level of PG [22:5/18:1] in the sample from the subject compared to the reference value is indicative of higher levels of EAT.

9. The method of claim 1, wherein the sample comprises serum or plasma obtained from the subject.

10. The method of claim 1, wherein the reference value is based on a mean level of the lipid biomarker in a control population of subjects.

11. The method of claim 1, wherein the determination of the level of the one or more lipid biomarkers in step (a) comprises using mass spectrometry.

12. The method of claim 1, wherein the determination of the level of the one or more lipid biomarkers in step (a) comprises using shotgun lipidomics.

13. The method of claim 1, further comprising diagnosing an unhealthy level of EAT based on the one or more lipid biomarkers in the sample from the subject.

14. The method of claim 1, wherein the subject is a human.

15. The method of claim 1, wherein the change in diet comprises a decrease in consumption of fat.

16. The method of claim 1, wherein the subject is a human or a non-human mammal, and the one or more nutritional products comprise at least one member selected from the group consisting of food products, drinks, pet food products, food supplements, nutraceuticals, food additives and nutritional formulas.

17. The method of claim 1, wherein the subject has a cardiovascular disorder or metabolic disorder.

18. The method of claim 1, wherein the levels of the one or more lipid biomarkers in the sample compared to the reference values are indicative of a risk of developing a cardiovascular disorder or metabolic disorder.

19. The method of claim 18, wherein the cardiovascular disorder is at least one of coronary artery disease, atherosclerosis or hypertension.

20. The method of claim 18, wherein the metabolic disorder is at least one of impaired fasting glucose, insulin resistance or diabetes mellitus.

21. The method of claim 1, further comprising repeating step (a) after administering the change in diet to the subject; and then comparing the level of EAT to the level of EAT determined in step (b) for the subject.

22. The method of claim 21, further comprising performing an assessment of an effectiveness of the change in diet provided in step (c) in modulating the level of EAT in the subject.

* * * * *